United States Patent [19]
Ohloff et al.

[11] 4,372,881
[45] Feb. 8, 1983

[54] UNSATURATED ALICYCLIC COMPOUNDS, THEIR USE AS PERFUMING AND FLAVORING INGREDIENTS

[75] Inventors: Günther Ohloff; Wolfgang K. Giersch, both of Bernex, Switzerland

[73] Assignee: Firmenich SA, Geneva, Switzerland

[21] Appl. No.: 306,827

[22] Filed: Sep. 29, 1981

[30] Foreign Application Priority Data

Oct. 16, 1980 [CH] Switzerland .......................... 7729/80

[51] Int. Cl.$^3$ .......................... C07C 45/66; A61K 7/46
[52] U.S. Cl. ................................ 252/522 R; 426/538; 568/375; 252/174.11
[58] Field of Search ................ 568/375; 252/522 R; 426/538

[56] References Cited
U.S. PATENT DOCUMENTS 4,147,672   4/1979   Schulte-Elte .............. 252/522 R
4,334,098   6/1982   Mookherjee ............... 252/522 R Primary Examiner—John F. Niebling
Attorney, Agent, or Firm—Pennie & Edmonds

[57] ABSTRACT

Unsaturated alicyclic compounds of formula

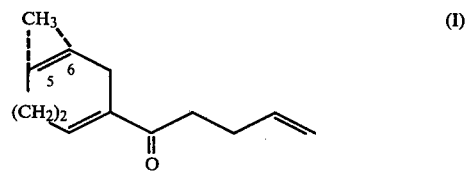

(I)

having a methyl radical bound to the carbon atom in position 5 or 6 of the ring, possess interesting perfuming and flavoring properties and consequently they can be used advantageously in the fragrance and flavor industry. They can develop various notes of green, flowery, fruity and fresh type.

5 Claims, No Drawings

UNSATURATED ALICYCLIC COMPOUNDS, THEIR USE AS PERFUMING AND FLAVORING INGREDIENTS

BRIEF SUMMARY OF THE INVENTION

The present invention relates to novel unsaturated alicyclic derivatives of pent-4-en-1-one of formula

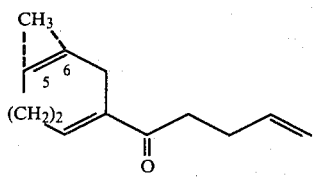

having a methyl radical bound to the carbon atom in position 5 or 6 of the ring as indicated by the dotted lines.

The invention provides further a process for the preparation of the compounds of formula (I), which process comprises reacting a carbonyl compound of formula

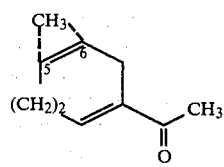

having a methyl radical bound to the carbon atom in position 5 or 6 of the ring, with an allyl halide in the presence of a strong base, and subsequently hydrolyzing the reaction product thus formed.

The invention relates also to a perfuming or flavouring composition comprising as active ingredient a compound of formula (I).

Finally, the invention provides a method to improve, enhance or modify the organoleptic properties of foodstuffs, beverages or pharmaceutical preparations, or the odorous properties of perfumes and perfumed products which method comprises the step of adding thereto an effective amount of a compound of formula (I).

BACKGROUND OF THE INVENTION

Various unsaturated alicyclic derivatives of pent-4-en-1-one are already known in the art. Among them, 1-(3,3-dimethyl-cyclohex-6-en-1-yl)-pent-4-en-1-one is certainly the compound presenting the most outstanding properties. It is characterized by a green, herbaceous odour reminiscent of galbanum oil and its odour strength is rarely encountered in perfumery (see e.g. Swiss Pat. No. 586,551).

DE-OS No. 2,917,450 discloses 1-(3,3-dimethyl-cyclopent-5-en-1-yl)-pent-4-en-1-one whose fragrance, though analogous to that of the above cited cyclohexenyl derivative, possesses a fruity tonality of plum and pear type.

Although the compounds of the invention bear a structural analogy with the above cited prior known derivatives, they possess in comparison with these a very distinct odour character. In actual experience, we have found that compounds (I) can reproduce odorous effects which could not be matched by the analogous cited ingredients.

PREFERRED EMBODIMENTS OF THE INVENTION

In the field of perfumery, compounds (I) are characterized by a powerful scent of green, fresh, fruity and flowery type reminiscent of the odour possessed by galbanum resinoid.

Due to these specific characters, compounds (I) can be advantageously utilized to manufacture compositions of flowery, fruity, green, herbaceous or woody type. They can also be used to perfume articles as varied as soaps, detergents, lotions, shampoos, cosmetics in general, such as body-milks or beauty creams, to which articles they confer a very pleasant fresh and natural note. In order to achieve these results, compounds (I) can be used in proportions varying from about 0.1 to 5% by weight based on the total weight of the perfumed article or perfume composition into which they are added. These proportions can be as high as 10% or even higher in those cases involving the preparation of perfume bases or concentrates.

In the field of flavours, compounds (I) are characterized by a strong, original gustative note of fruity type reminiscent of pineapple accompanied by a resinous and green note reminiscent of certain aspects of the aroma of galbanum oil. Compounds (I) can be utilized advantageously to flavour foodstuffs and beverages of different nature, namely fruity and green, as well as pharmaceutical preparations and tobacco. They can be used on their own as flavouring agents, or in compositions comprising one or more other flavouring coingredients, in the form of diluted or concentrated solutions in the solvents commonly employed for this purpose, such as ethanol, triacetine and diethylene glycol. They can also be employed on solid supports, for instance on dextrines or gum arabic. Interesting gustative effects can be achieved by using compounds (I) in concentrations of the order of 0.01 to 10 ppm (parts per million) by weight based on the weight of the flavoured material.

The compounds of formula (I) are new chemical entities. According to the process of the invention, they can readily be obtained from a carbonyl compound of formula

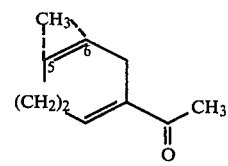

having a methyl radical bound to the carbon atom in position 5 or 6 of the ring, by reacting it with an allyl halide, e.g. allyl chloride, bromide or iodide, in the presence of a strong base, and subsequently hydrolyzing the reaction product thus formed.

The first step of the process of the invention is effected according to usual techniques, for instance in a manner analogous to that described in Swiss Pat. No. 590,810. Suitable strong bases include an alkali metal alkoxide, e.g. sodium methoxide, an alkyl-lithium or a secondary amine lithium salt, for instance lithium di-isopropylamide. The reaction can be carried out in the presence of an inert organic solvent, though this condition is not critical for obtaining the end product in good yields.

The subsequent hydrolysis can also be carried out in analogy with known techniques. Suitable hydrolyzing agents include e.g. hydrochloric, sulfuric or aqueous phosphoric acid. Carbonyl compounds (II), used in the process described above as starting materials, can be synthesized from 1,5- or 1,6-dimethyl-cycloocta-1,5-diene by ozonolysis and subsequent hydrolysis, according to the following reaction scheme:

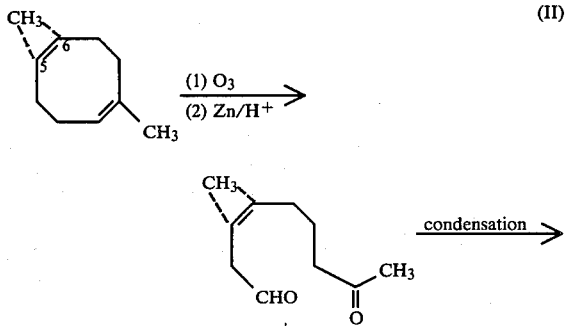

Due to the fact that starting dimethyl-cyclooctadiene is available as a rule under the form of an isomeric mixture of 1,5- and 1,6-dimethyl derivatives, the compounds of formula (II) are obtained as corresponding mixtures of isomers. If desired, each of the constituents of said mixtures can be separated, e.g. by vapour phase chromatography, before conversion into desired end-products.

In an analogous way, starting from a mixture of 5- and 6-methylcyclohepta-1,5-dien-1-yl methyl ketone, there is obtained a corresponding mixture of the compounds of formula (I), whose constituents can be isolated by vapour chromatography or by fractional distillation by making use of a column with high separation power. For practical and economical reasons however, the mixtures as obtained by the process described above, can be utilized directly in accordance with the invention.

The invention is illustrated in a more detailed manner by the following examples wherein the temperatures are indicated in degrees centigrade.

EXAMPLE 1

1-(5-Methyl-cyclohepta-1,5-dien-1-yl)-pent-4-en-1-one
and
1-(6-methyl-cyclohepta-1,5-dien-1-yl)-pent-4-en-1-one 5.0 g of 80:20 mixture of 5-methyl-cyclohepta-1,5-dien-1-yl methyl ketone and 6-methyl-cyclohepta-1,5-dien-1-yl methyl ketone and 6.0 g of ethyl oxalate have been added under nitrogen atmosphere to a cooled solution (−10°) of 0.9 g of sodium in 25 ml ethanol. Once the addition was over, the reaction mixture was gradually warmed to about 70°, whereupon 3.6 g of allyl bromide were added thereto while the heating was carried on for 10 more minutes.

The mixture was poured onto ice and acidified with diluted hydrochloric acid and finally extracted with ether. After the usual workup of the organic extracts (washing with 10% aqueous $NaHCO_3$, drying over $Na_2SO_4$, evaporation and fractional distillation), 3.16 g (yield 50%) of an 80:20 mixture of 1-(5-methyl-cyclohepta-1,5-dien-1-yl)-pent-4-en-1-one and 1-(6-methyl-cyclohepta-1,5-dien-1-yl)-pent-4-en-1-one were collected; b.p. 78°/0.05 Torr.

The isomeric mixture obtained above can be used as such in accordance with the invention.

Pure analytical samples were isolated from the mixture by vapour phase chromatography (CARBOWAX 20 M-3 m-180°).

1-(5-methyl-cyclohepta-1,5-dien-1-yl)-pent-4-en-1-one

NMR (90 MHz): 1.68 (3H, s); 3.08 (2H, d, J=5 Hz); 4.9–5.13 (2H, m); 5.46 (1H, m); 5.6–6.06 (1H, m); 6.97 (1H, t, J=6 Hz) δ ppm;

MS: M+ =190(11); m/e: 175(34), 162(100), 147(37), 135(87), 107(83), 91(92), 79(78), 55(80), 41(42), 29(45).

1-(6-methyl-cyclohepta-1,5-dien-1-yl)-pent-4-en-1-one

NMR (90 MHz): 1.74 (3H, s); 3.14 (2H, broad s); 4.95–5.13 (2H, m); 5.46 (1H, m); 5.6–7.07 (1H, m); 6.95 (1H, t, J=6 Hz) δ ppm;

MS: M+ =190(14); m/e: 175(13), 162(100), 147(33), 135(63), 107(91), 91(87), 79(74), 55(84), 41(38), 29(44).

The mixture of 5- and 6-methyl-cyclohepta-1,5-dien-1-yl methyl ketone, used as starting materials in the above described process, was obtained as follows:

a. A flow of ozone was passed through a solution kept at 0° of 30 g of an 80:20 mixture of 1,5- and 1,6-dimethyl-cycloocta-1,5-diene in 300 ml of petrolether 80/100 (time: 2 hours, absorption: 3.7 g $O_3$). 25 g of zinc powder and 25 g of glacial acetic acid were then added thereto under stirring and the resulting mixture was kept at room temperature for 16 h. After decantation, the organic phase was separated, washed with water until neutrality, dried over $Na_2SO_4$ and finally distilled to give 25 g (yield about 65%) of a 80:20 mixture of 4-methyl-8-oxo-non-4-en-1-al and 5-methyl-8-oxo-non-4-en-1-al as indicated by vapour phase chromatography.

b.p. 70°–100°/0.2 Torr;

IR: 2700, 1720 cm$^{-1}$;

NMR (60 MHz): 1.7 (3H, d, J=1 Hz); 2.17 (3H, s); 5.12 (1H, m): 9.8 (1H, t, J=1 Hz) δ ppm;

MS: M+ =168(1); m/e: 150(7), 107(13), 92(9), 81(27), 67(11), 55(17), 43(100).

b. A mixture of 34.4 g of the product obtained in accordance with the method described sub letter a. above, in 700 ml of methanol was mixed with 100 ml of a 5% aqueous solution of NaOH and kept under stirring for 24 hours at room temperature. After evaporation of the excess of methanol, the mixture was diluted with ether, washed with water until neutrality, evaporated and finally distilled to give 13.5 g (yield ca. 45%) of an 80:20 mixture of 5- and 6-methyl-cyclohepta-1,5-dien-1-yl methyl ketone as indicated by vapour phase chromatography;

b.p. 40°–70°/0.05 Torr;

An analytical sample of each of the two products was obtained by preparative vapour phase chromatography.

5-methyl-cyclohepta-1,5-dien-1-yl methyl ketone

IR: 1660 cm$^{-1}$;

NMR (90 MHz): 1.66 (3H, broad s); 2.3 (3H, s); 2.92 (2H, d, J=6 Hz); 5.28 (1H, t, J=6 Hz); 6.97 (1H, t, J=5.5 Hz) δ ppm MS: M+ =150(27); m/e: 135(43), 122(53), 107(41), 91(45), 79(38), 43(100).

6-methyl-cyclohepta-1,5-dien-1-yl methyl ketone

IR: 1660 cm$^{-1}$;

NMR (90 MHz): 1.58 (3H, broad s); 2.3 (3H, s); 3.13 (2H, broad s); 5.46 (1H, m); 6.94 (1H, t, J=5.5 Hz) δ ppm;

MS: M+ =150(43); m/e: 135(25), 122(37), 107(54), 91(45), 79(39), 43(100).

EXAMPLE 2

A base flavouring composition of fruity type was prepared by mixing the following ingredients (parts by weight):

| Ingredient | Parts by weight |
|---|---|
| Vanilline | 20 |
| Sweet orange oil | 40 |
| Lemon oil | 10 |
| Amyl acetate | 20 |
| Butyl acetate | 30 |
| Ethyl propionate | 30 |
| Ethyl butyrate | 50 |
| Ethyl valerate | 20 |
| Ethyl oenanthate | 40 |
| Benzyl alcohol | 200 |
| Propylene glycol | 540 |
| Total | 1000 |

A "control" and a "test" composition were prepared by making use of the thus prepared base composition:

|  | A (control) | B (test) |
|---|---|---|
| Base composition | 100 | 100 |
| Compound according to Example 1[(1)] | — | 2 |
| 95% Ethanol | 900 | 898 |
|  | 1000 | 1000 |

[(1)]10% solution of isomeric mixture (b.p. 78°/0.05 Torr) in 95% ethanol.

Compositions A and B were added to an acidic sugar syrup at a concentration of 1 g of composition for 1 l of syrup, and the resulting beverages were tasted by a panel of trained flavourists. Their comments were the following:

- syrup flavoured with composition A: fruity note of pineapple type, slightly green, resinous.
- syrup flavoured with composition B: fruity note of "tutti-frutti" type.

An analogous gustative effect was obtained by replacing the isomeric mixture of above example by an identical quantity of each of its discrete ingredients.

EXAMPLE 3

0.1 g of the compound obtained in accordance with Example 1 above (isomeric mixture having b.p. 78°/0.05 Torr) was incorporated into an olfactively neutral commercial soap paste. This perfumed material was then used to manufacture toilet soap bars which were subjected to an evaluation by a panel of perfumers. The perfumed samples presented an agreeable very natural fragrance of flowery-green type.

A similar effect was observed by replacing the mixture of isomers with identical quantities of its discrete components.

EXAMPLE 4

A base perfume composition of Eau de Cologne type was prepared by mixing the following ingredients (parts by weight):

| Lemon oil | 250 |
|---|---|
| Bergamot oil | 300 |
| Orange oil | 150 |
| Petitgrain Bigarade | 100 |
| Neroli Bigarade | 20 |
| Lavender oil | 70 |
| White thyme oil | 10 |

By diluting the above composition in 95% ethanol at a concentration of 3%, there was obtained a "classical" Eau de Cologne. The addition to 100 g of the Eau de Cologne of 1.5 g of a 10% ethanolic solution of the compound obtained according to Example 1 (isomeric mixture having b.p. 78°/0.05 Torr), conferred a very elegant and natural character thereto.

A similar result was achieved by replacing the isomeric mixture by one of its components, i.e. 1-(5-methyl-cyclohepta-1,5-dien-1-yl)-pent-4-en-1-one and 1-(6-methyl-cyclohepta-1,5-dien-1-yl)-pent-4-en-1-one.

EXAMPLE 5

A base perfume composition was prepared by mixing together the following ingredients (parts by weight):

| Benzyl pivalate | 200 |
|---|---|
| Terpenyl acetate | 150 |
| Elemol | 100 |
| Linalol | 100 |
| Dihydromircenol 10%* | 80 |
| α-Hexyl-cinnamic aldehyde | 60 |
| Phenyl-ethyl pivalate | 40 |
| Dimethyl octanol | 30 |
| Methyl cyclopentylidene-acetate[(1)] 1%* | 30 |
| Citronellyl acetate | 20 |
| Octanal 10%* | 20 |
| Decanal 10%** | 20 |
| Nonanal 10%* | 10 |
| Undecanal 10%* | 10 |
| Dimethyl-cyclohexenyl-carbaldehyde | 10 |
| Total | 880 |

[(1)]CYCLOPIDENE : origin Firmenich SA, Geneva - Switzerland - see Swiss Patent No. 616,077.
*in dipropylene glycol.

The above base possesses a flowery-fresh odour and is particularly adapted to perfume hair care articles such as e.g. shampoos or hair lotions.

By adding to 88 g of the above base, 12 g of a 10% solution of the product obtained according to Example 1 (isomeric mixture having b.p. 78°/0.05 Torr) in dipropyleneglycol, a novel composition possessing a greener and fresher scent than the base composition was obtained. Its odour was also richer and stronger.

A similar effect was obtained by replacing the isomeric mixture by one of its discrete components.

What we claim is:

1. A compound of formula $$\text{(I)}$$

having a methyl radical bound to the carbon atom in position 5 or 6 of the ring.

2. 1-(5-Methyl-cyclohepta-1,5-dien-1-yl)-pent-4-en-1-one.

3. 1-(6-Methyl-cyclohepta-1,5-dien-1-yl)-pent-4-en-1-one.

4. Perfuming composition which comprises as active ingredient an effective amount of a compound of formula (I) as defined in claim 1.

5. Flavouring composition which comprises as active ingredient an effective amount of a compound of formula (I) as defined in claim 1.

* * * * *